United States Patent [19]

Ender et al.

[11] Patent Number: 5,516,778
[45] Date of Patent: May 14, 1996

[54] METHOD FOR IMPROVING TISSUE ANTIOXIDANT STATUS

[75] Inventors: Ferenc Ender; József Fürész; László Rosivall; Katalin Schweitzer, all of Budapest, Hungary

[73] Assignee: Chinoin Gyogyszer- Es Vegyeszeti Termekek Gyara Rt., Budapest, Hungary

[21] Appl. No.: 282,752

[22] Filed: Jul. 29, 1994

[30] Foreign Application Priority Data

Aug. 2, 1993 [HU] Hungary .................................. 2229/93

[51] Int. Cl.⁶ .......................... A61K 31/52; A61K 31/47
[52] U.S. Cl. ........................... 514/263; 514/264; 514/309
[58] Field of Search ..................................... 514/263, 264, 514/309

[56] References Cited

PUBLICATIONS

Obstet. Gynecol. 75 (6), 1990, pp. 147–157.
Ellis, H., "The Cause and Prevention of Postoperative Peritoneal Adhesion", Surg. Gynec. Obstet, 133: 497 to 511 (Sep. 1971).
Sawyers et al, "The Acute Abdomen. In: The Surgical Clinics of North America", 68, (2), 353 to 364 (Apr. 1988).
Soliman, M. H. et al, "Pentoxifylline Improves Tissue Oxygenation Following Anaesthesia and Operation", Crit. Care Med. 15, 93 to 94 (1987).
CA 118:116687, Kumar et al., 1992.
CA 121:148666, Kang et al., 1993.

*Primary Examiner*—Kimberly Jordan
*Attorney, Agent, or Firm*—Herbert Dubno

[57] ABSTRACT

The invention relates to a method of using 3,7-dihydro-3, 7-dimethyl-1-(5-oxohexyl)-1H-purine-2,6-dione (generic name:pentoxifylline) and/or 1-(3',4'-diethoxybenzyl)-6,7-diethoxy-3,4-dihydroisoquinolinium theophylline-7-acetate (Depogen) or monohydrate thereof to improve mammalian tissue antioxidant status. This status plays an important role in complications, occurring as a consequence of pathologically developed or artificially established anastomoses, particularly anastomosis of oesophagus and colon since these organs possess a very weak antioxidant protective system.

4 Claims, 5 Drawing Sheets

FIG. 2 Effect of Trental treatment on the TBARS content of the region of operation Effect of Trental on the inflammatory reaction of the peritoneum PRI = Peritoneal reaction index

METHOD FOR IMPROVING TISSUE ANTIOXIDANT STATUS

FIELD OF THE INVENTION

The invention relates to a pharmaceutical composition containing as active ingredient 3,7-dihydro- 3,7-dimethyl-1-(5-oxohexyl)-1H-purine-2,6-dione and/or 1-(3',4'-diethoxybenzyl)-6,7-diethoxy-3,4-dihydroisoquinolinium theophylline-7-acetate or its monohydrate and a process for the preparation thereof. According to this process 3,7-dihydro-3,7-dimethyl-1-(5-oxo-hexyl)-1-H-purine-2,6-dione and/or 1-(3',4'-diethoxybenzyl)-6,7-diethoxy-3,4-dihydroisoquinolinium theophylline-7-acetate or its monohydrate prepared in a manner known per se are mixed together with filling, diluting agents and other auxiliaries (additives) commonly used in drug manufacture and the mixture obtained is converted to a pharmaceutical composition useful for improving the tissue antioxidant status.

Furthermore, the invention also relates to the use of 3,7-dihydro-3,7-dimethyl-1-(5-oxohexyl)-1H-purine-2,6-dione and/or 1-(3'4'-diethoxybenzyl)-6,7-diethoxy-3,4-dihydroisoquinolinium theophylline-7-acetate or its monohydrate as active ingredient for the preparation of a pharmaceutical composition useful for improving the tissue antioxidant status; as well as to a method of improving the tissue antioxidant status, which comprises using a therapeutically effective amount of 3,7-dihydro-3,7-dimethyl-1-(5-oxohexyl)-1H-purine-2,6-dione and/or 1-(3',4'-diethoxybenzyl)-6,7-diethoxy-3,4-dihydroisoquinolinium theophylline-7-acetate or the monohydrate thereof.

BACKGROUND OF THE INVENTION

The preparation of 3,7-dihydro-3,7-dimethyl-1-(5-oxohexyl)-1H-purine-2,6-dione (TRENTAL$^R$; generic name: pentoxifylline) and 1-(3',4'-diethoxybenzyl)-6,7-diethoxy-3,4-dihydroisoquinolinium theophylline-7-acetate (Depogen) or its monohydrate, respectively is described inter alia in the following patent specification: GB No. 1,079,267; German No. 2,234,202; Czechoslovak No. 164,343; as well as Hungarian No. 167,246 and Hungarian No. T/42449 made open to public inspection.

It is known that both pentoxifylline and Depogen improve the microcirculation of the blood [Angiology 36, pages 2226–2234 (1984); as well as Hungarian patent specification No. 197,207].

Anastomosis insufficiency is the most severe complication of surgical interventions made in the gastrointestinal system. In spite of the modern suture techniques and up-to-date antibiotic treatments, the occurrence of this complication is very frequent, and significantly prolongs the period of hospital treatment and increases the rate of mortality.

Complications most frequently occur at anastomoses established on various regions of the oesophagus and on the left-side colon. This has partly anatomical, circulation and microbiological reasons; however, in addition, an important role may be attributed in the development of complications to the fact that both the oesophagus and colon possess a very weak antioxidant protective system.

It has been proved by a number of experimental observations that the early phase of the healing process of intestinal anastomosis can be characterized by an early collagenolysis, i.e. by a rapid decrease in the collagen concentration. The tensile strength of anastomosis decreases proportionally to the collagen decomposition in the early postoperative days and a definitive pressure increase is started by the building-up of the new collagen skeleton only after 6 to 7 days. The early wound separation in the line of anastomosis occurs in this period.

In addition to the surgical techniques, the drug-assisted healing of the anastomosis is an important task. In clinical practice no drug process is known, which has been aimed to directly promote the healing of anastomosis. Clinical experiences show that in programmed surgery the occurrence of complications is diminished but not completely eliminated by arrangement of the haematological status of the patient, appropriate protein and electrolyte supply or preparation of the gastrointestinal system by antibiotics.

Another frequent complication of anastomosis surgery appears in the formation of adhesions. The essential problem of inhibiting adhesion is to retain the integrity of anastomosis prepared in the abdominal cavity. Although good adhesion-inhibitory properties of some compounds are known, their use abruptly increases the rate of anastomosis insufficiencies [Obstet. Gynecol. 75 (6), (1990)].

In the experiments of Steinleitner and coworkers, adhesions of abdominal cavities were prevented by the administration of pentoxifylline. A dose of 25 mg/kg/12 hours decreased the adhesions induced by tissue destruction model and inhibited the repeated formation of previously developed and surgically solved adhesions. The good results were explained by the effects of pentoxifylline modulating leukocyte functions.

Based on the negative effects of previously known adhesion inhibitors on the healing of anastomosis, the use of pentoxifylline during the perioperative period is presumably contraindicated because of the occasionally occurring anastomosis insufficiency.

SUMMARY OF THE INVENTION

In opposition to this, it has been found that, when administered in a suitable dose, pentoxifylline or Depogen or its monohydrate, respectively are suitable to accelerate the healing process of anastomoses by improving the tissue antioxidant status beside other potential activities and, in addition, they retain their good adhesion-inhibitory effect.

Our experiments were carried out on male Wistar rats of 200 to 250 g body weight under pentobarbital anaesthesia [50 mg/kg intraperitoneally (i.p.)]. After median laparotomy under non-sterile conditions, the left-half colon was isolated, dissected in its whole cross-section and a mucous membrane-free end-to-end anastomosis was established.

The animals were fasted before the operation for 2 days and after the operation for 1 day but allowed to drink liquid ad libitum. The control group received 0.1 ml/100 g of physiological saline for 24 or 12 hours, respectively before the surgical intervention. Simultaneously, the first treatment group received 0.25 mg/100 g of pentoxifylline intraperitoneally (i.p.) and this dose was repeated altogether 4 times every 12 hours following the operation. The animals of the second treatment group were simultaneously treated with 2 mg/100 g of pentoxifylline i.p.

The tissue antioxidant status was investigated as follows.

1. Before working up, the organs taken out from the animals and frozen were homogenized in a 5-fold volume (ml) of recovering liquid related to the wet weight (g).

The post-treatment alteration of superoxide anion-scavenging capability (SOD-like effect) was determined in previous experiments. The development of lipid peroxidation was characterized by the amount of the thio-barbituric acid reactive substances (TBARS) formed.

The frozen samples were worked up in various intervals. After homogenization the measurements of activity were always carried out in the same intervals.

Succession order of the examinations:
1. Determination of organ weights
2. Determination of amount of the recovering liquid, homogenization
3. Centrifuging at 6000 rpm (rotation/min)
4. Determination of TBARS value within 6 hours
5. Measurement of the SOD-like effect on a 24-hour sample
6. Determination of protein within 24 hours.

DETERMINATION OF THIOBARBITURIC ACID-REACTIVE SUBSTANCES (TBARS)

[M. Uchiyama and M. Mihara: "Determination of Malondialdehyde Precursor in Tissues by Thiobarbituric Acid Test", Anal. Biochem. 86, pages 271–278 (1978)].

This measurement was carried out on a homogenate of 10% containing 1.2% of potassium chloride. After acidifying, incubating with thiobarbituric acid (TBA) solution for 45 minutes and adding butanol, the mixture was centrifuged. The determination was performed at 535 nm on the butanol phase.

DETERMINATION OF THE SOD-LIKE EFFECT

[H. P. Mishra and I. Fridovich: "The Role of Superoxide Anion in the Autooxidation of Epinephrine and a Simple Assay for Superoxide Dismutase", J. Biol. Chem. 247, pages 3170–3175 (1972); as well as B. Matkovics et al.: "Quantitative Determination of Peroxide Metabolism Enzymes SOD, Peroxide, and Catalase in Laboratory Materials", Lab. Diagn. 91 (4), (1977)].

The organ was homogenized in 5-fold volume of distilled water related to the wet organ weight (g) and centrifuged. After adding the tissue homogenate to an epinephrine solution of pH 9.6, the inhibition of epinephrine-adrenochrome autooxidation was measured.

In the case of an enzyme preparation, the 50% inhibition means an enzyme unit.

Protein was determined according to O. H. Lowry et al. [J. Biol. Chem. 193, pages 265–275 (1951)].

The following results were obtained.

The SOD-like activity decreased in the operated control group (0.68 U/mg of protein) treated with physiological saline in comparison to the biological control group (3.59 U/mg of protein) in the first hour; whereas the SOD-like activity of the pre-anastomosis intestinal segment (8.03 U/mg of protein) of the group operated and treated with pentoxifylline exceeded the SOD-like activity of the biological control group (3.59 U/mg of protein).

Figure 1:
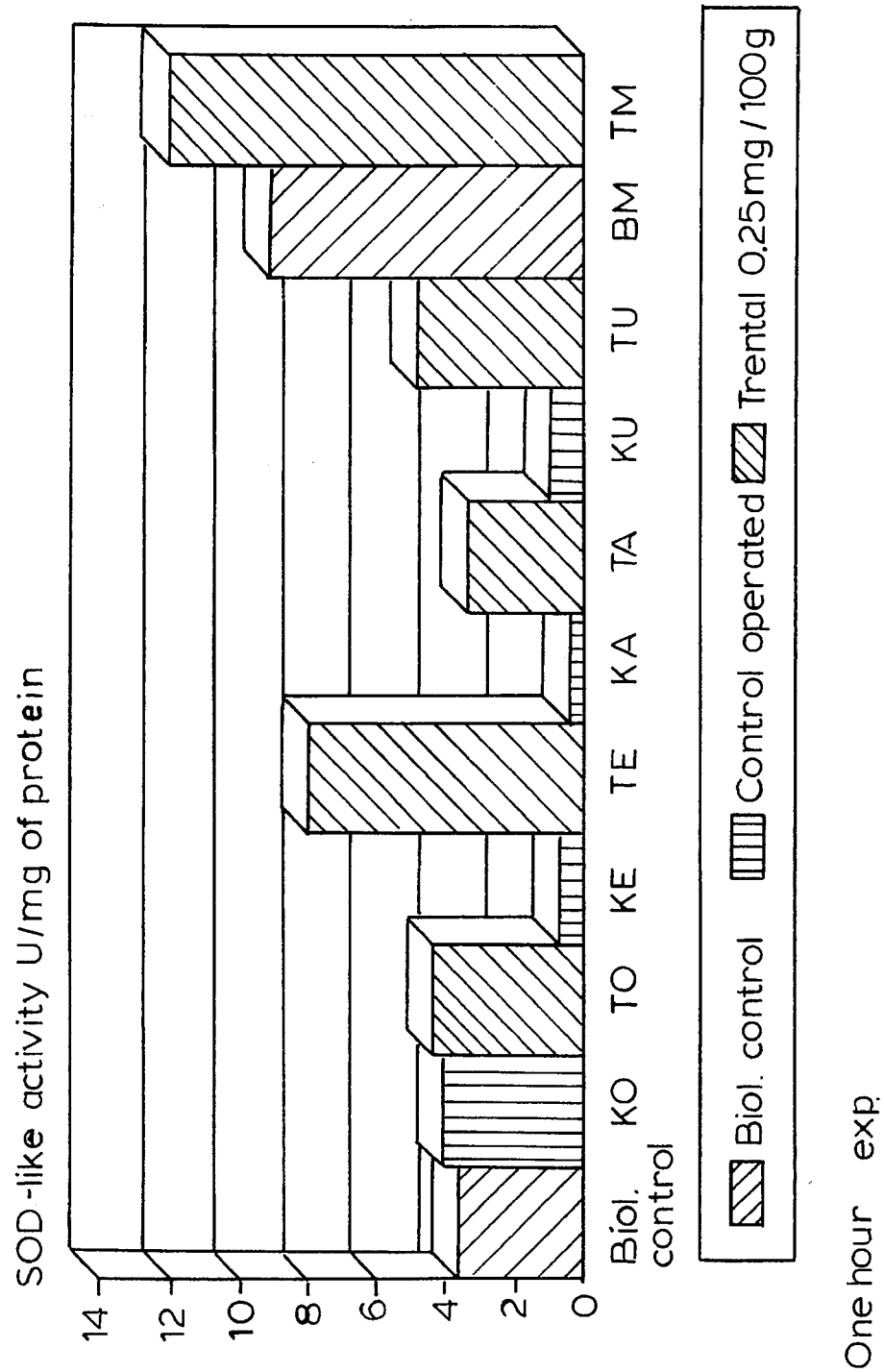
FIG. 1 is a series of bar graphs comparing the effect of pentoxifylline on the superoxide dismutase (SOD) —like activity in the rat colon and liver with the SOD-like activity in untreated control groups.

On the after-anastomosis intestine segment of the treatment group, the endogenic scavenger activity (4.81 U/mg of protein) was nearly 5-times as high as that of the control group (0,95 U/mg of protein) (FIG. 1).

The rate of inhibition over 10% was found to be 74% in the pentoxifylline-treated group, 25% in the biological control group and 27% in the operated control group.

Figure 2:
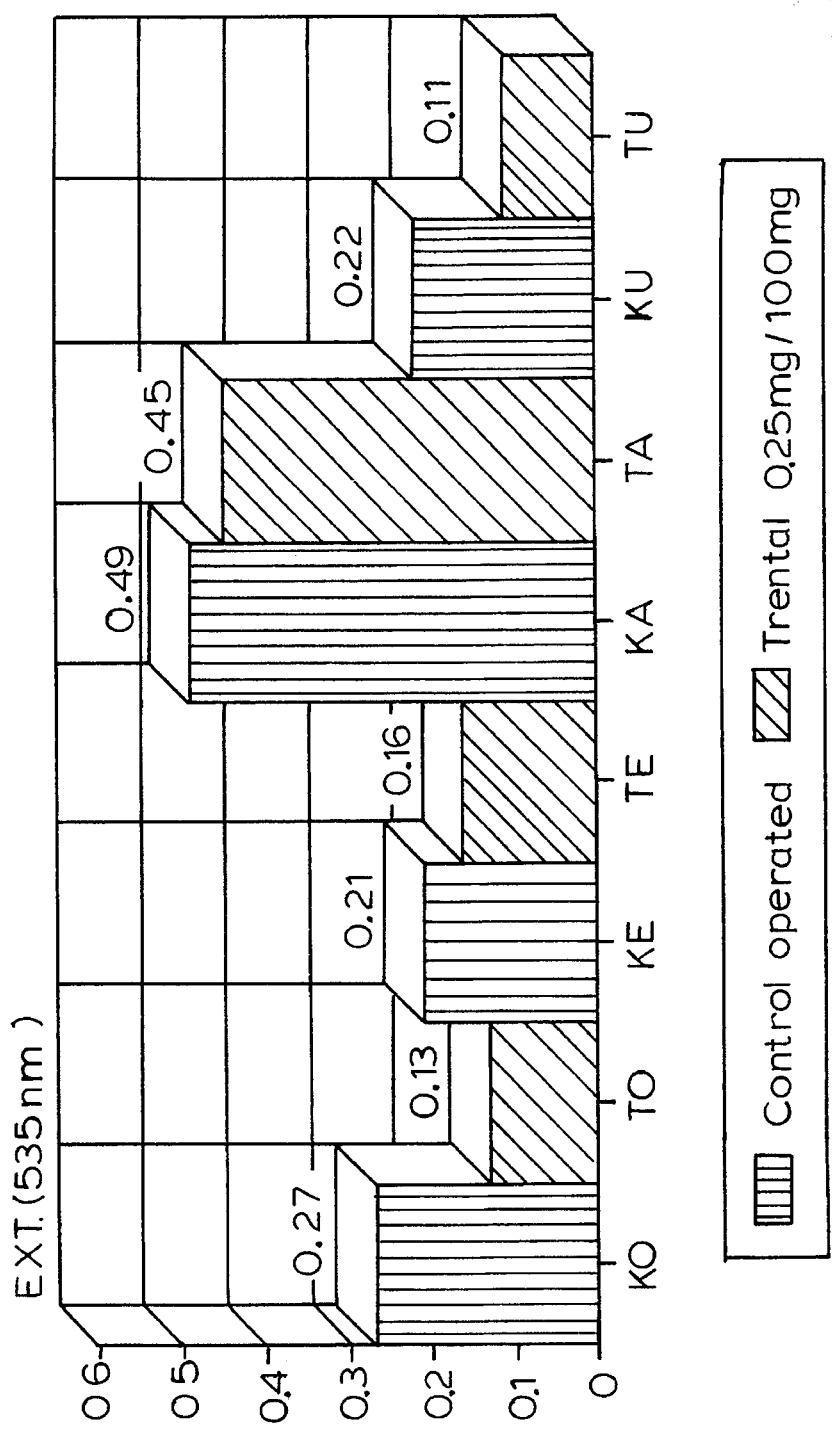
FIG. 2 is a series of bar graphs comparing the effect of pentoxifylline on the level of lipid peroxidation as determined by the amount of thiobarbituric acid-reactive substances (TBARS) in the rat colon with the levels in untreated control groups.

The lipid peroxidation (TBARS content) was decreased in all samples under the effect of pentoxifylline. This decrease was particularly significant in the intestinal segment remote from the anastomosis and in the segment directly following the site of the anastomosis (FIG. 2).

The above data confirm that pentoxifylline treatment exerts a positive influence on the antioxidant status.

As it is known from the literature, the healing of surgical wounds is significantly effected by the tissue antioxidant status. Thus, the healing of anastomosis was studied as described hereinafter.

The healing ability of anastomosis was characterized by the anastomosis bursting pressure (ABP) measured on the 1st, 2nd and 5th days in animals over-anaesthetized by pentobarbital [K. A. Houston: "Fibrin Sealant in High-Risk Colonic Anastomoses", Arch. Surg. 123, pages 230–234 (1988)].

The peritoneal reaction index (PRI) was used to determine the adhesion or the tissue reaction, respectively. ["Effect of Captopril on the Development of Experimentally Established Adhesions in Abdominal Cavity" (in Hungarian); Magyar Sebészet 45, pages 57–60 (1992)].

The following results were obtained.

Figure 3:
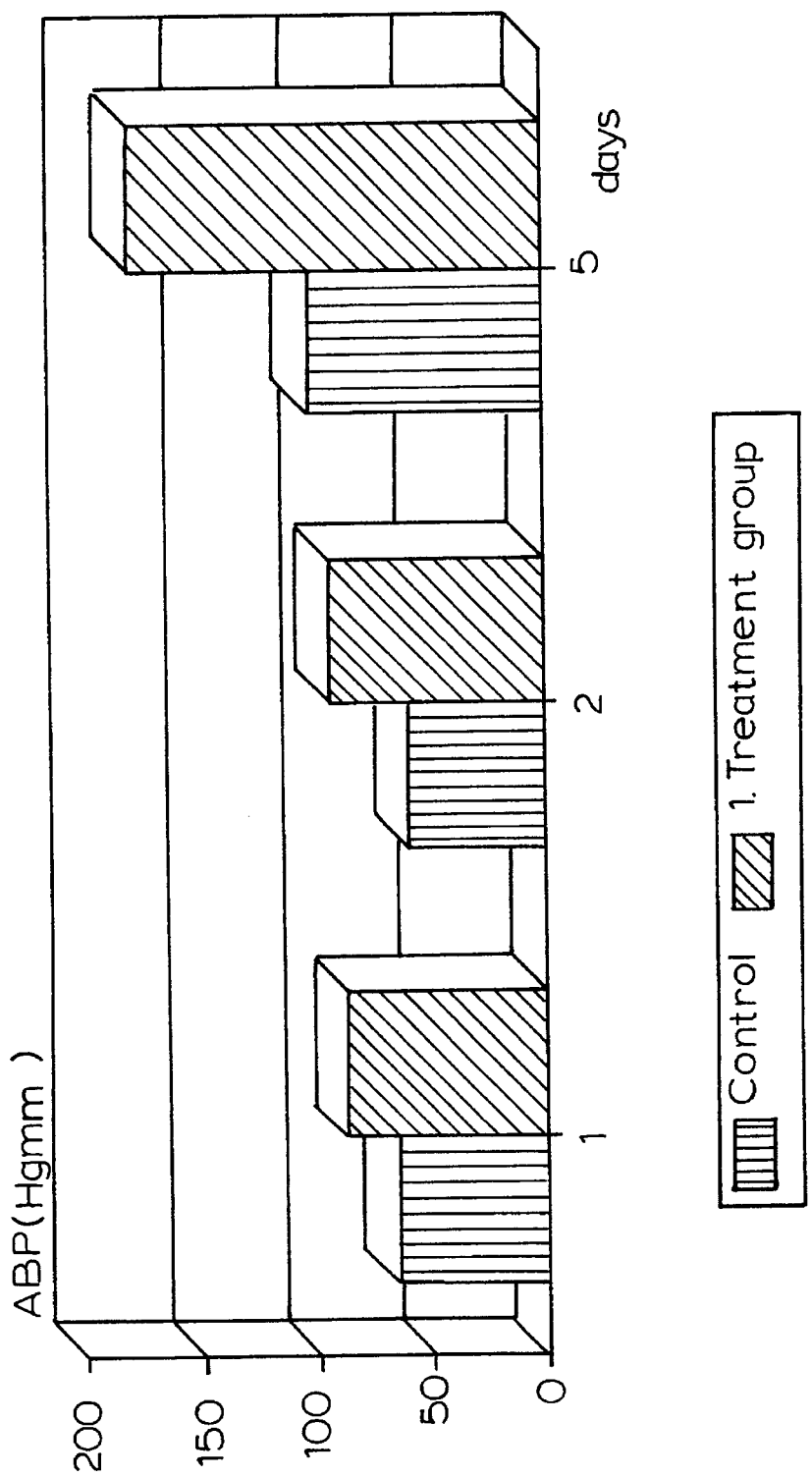
FIG. 3 is a series of bar graphs comparing the anastomosis bursting pressure (ABP) following i.p. treatment of rats with a dose of pentoxifylline of 0.25 mg/100 g versus that in untreated control after 1, 2 and 5 days.

Under effect of an i.p. treatment with 0.25 mg/100 g of pentoxifylline, the ABP value in the treated group (94 Hgmm) on the 2nd day was significantly higher than that of the control group (60 Hgmm). On the 5th day the ABP value of the pentoxifylline-treated group (180 Hgmm) reached 81% of the pressure value of the normal colon (218 Hgmm), whereas the pressure value of the control group (103 Hgmm) remained significantly lower in comparison to that of the treated group (180 Hgmm) (FIG. 3).

Figure 4:
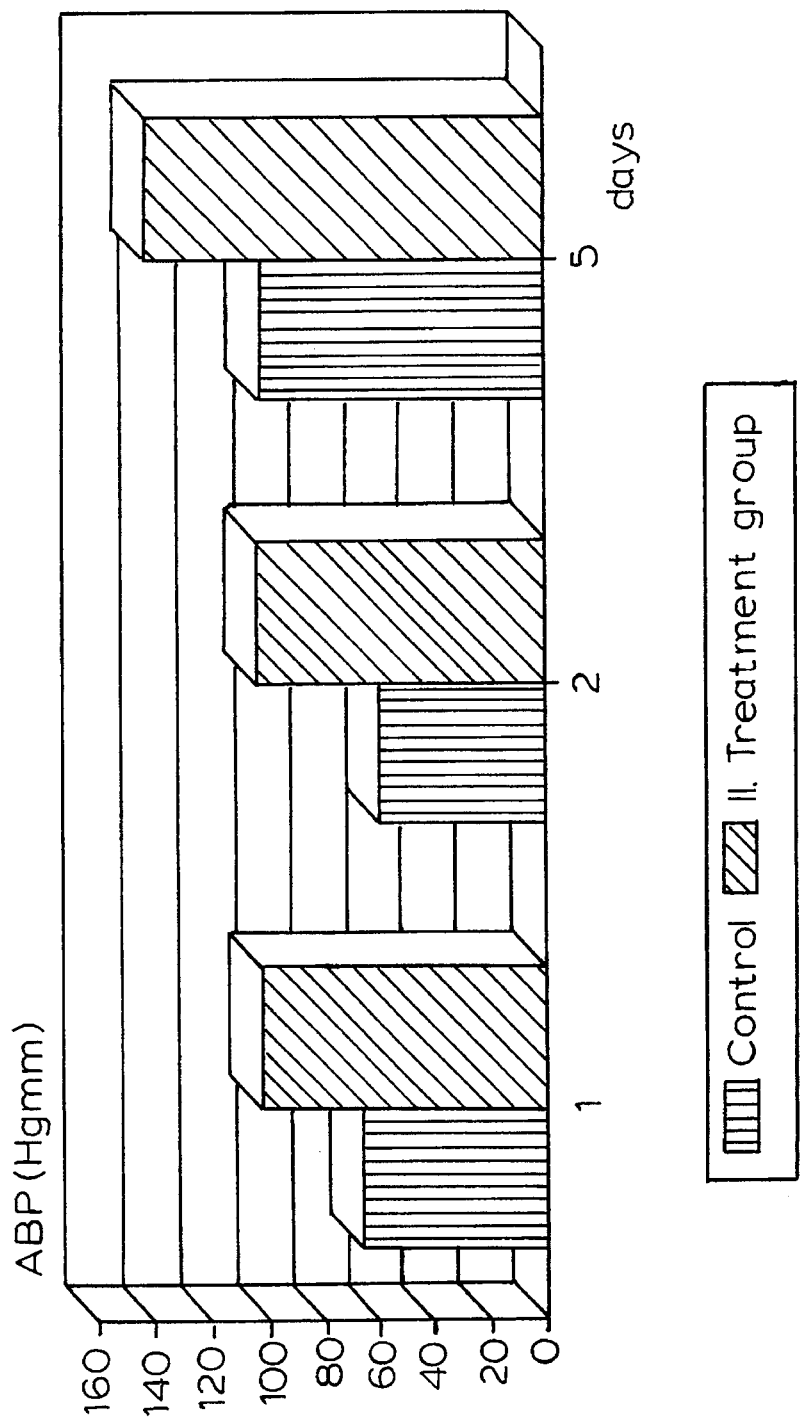
FIG. 4 is a series of bar graphs comparing the anastomosis bursting pressure (ABP) following i.p. treatment of rats with a dose of pentoxifylline of 2 mg/100 g versus that in untreated control after 1, 2 and 5 days.

Upon the effect of a treatment with 2 mg/100 g of pentoxifylline, the ABP value of the treated group (102 Hgmm) on the 1st day was significantly higher than that of the control group (66 Hgmm); this difference could be measured on the 2nd postoperative day, too (FIG. 4).

It can be stated from the above experimental results that the favorable change in the antioxidant effect was accompanied by the abbreviation of healing time of the surgical wound.

Figure 5:
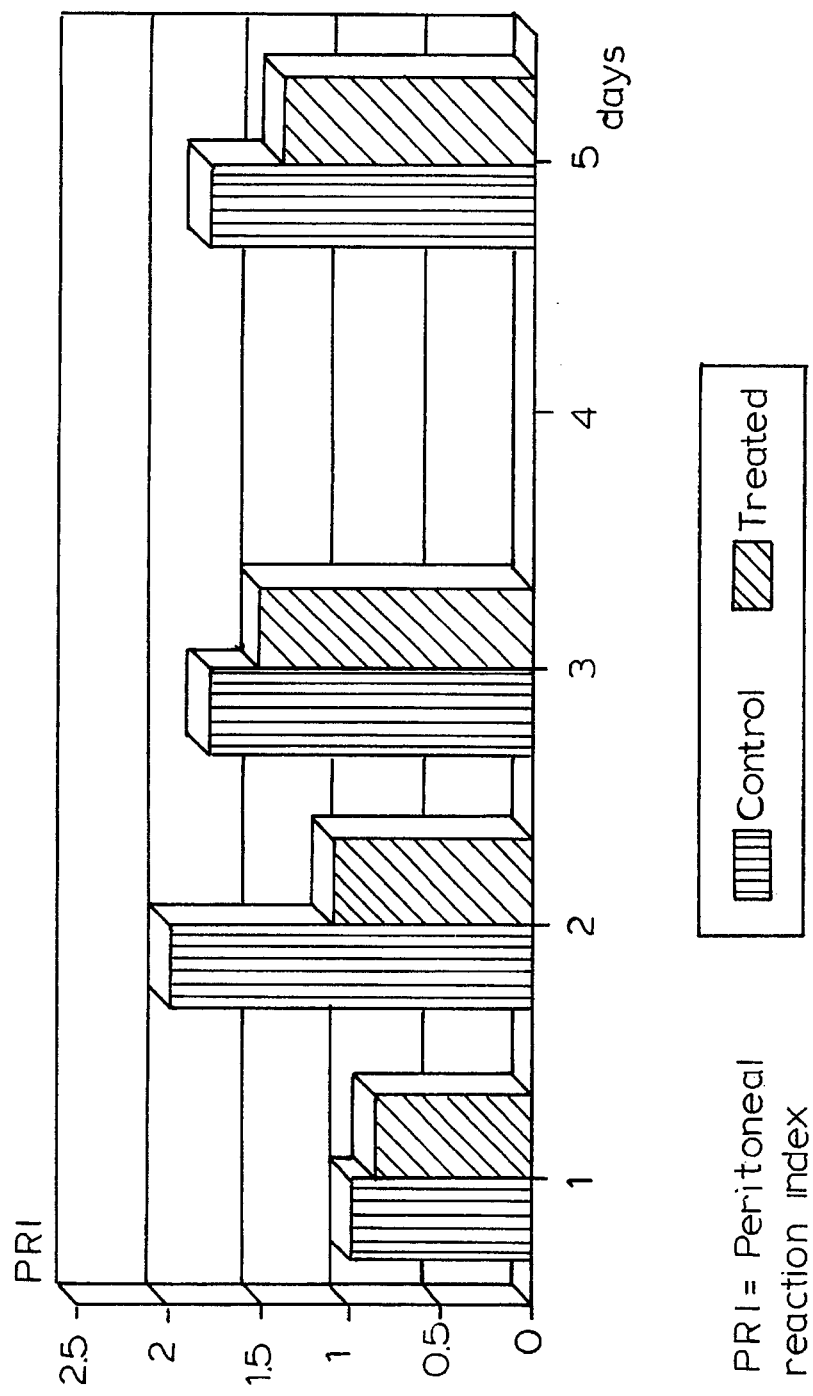
FIG. 5 is a series of bar graphs comparing the peritoneal inflammatory reaction index (PRI) following the i.p. treatments of rats with pentoxifylline versus the PRI in untreated controls.

The PRI value calculated on the basis of scores given for the peritoneal inflammatory reaction significantly increased in the control group on the 2nd day (2.0) in comparison to the 1st day (1.0). This increase did not occur in the treated group therefore, the inflammatory reaction of the treated group (1.1) was found to be significantly lower than that of the control group (2.0) on the 2nd day (FIG. 5).

Summing up, our experimental results show that, pentoxifylline and Depogen, respectively abbreviate the healing period (time) of the anastomosis and decrease the development of adhesions by improving the tissue antioxidant status.

Abbreviations and signs used in the Figures have the following meanings:
ABP: Anastomosis bursting pressure
PRI: Peritoneal reaction index
TBARS: Thiobarbituric acid-reactive substances
Control operated: Operated, untreated group
Treatment (treated) group: Operated group treated with pentoxifylline
Pseudo-operated group: Intestinal anastomosis was not established after opening the abdominal wall
Biol. control: Biological control group without operation
KO: Control group with intact colon
KE: Control group, pre-anastomosis segment
KA: Control group, anastomosis
KU: Control group, after-anastomosis segment
Trent group: Operated group treated with pentoxifylline
TO: Operated group with intact colon treated with pentoxifylline
TE: Operated group treated with pentoxifylline, pre-anastomosis segment
TA: Operated group treated with pentoxifylline, anastomosis segment
TU: Operated group treated with pentoxifylline, after-anastomosis segment
BM: Biological group, liver
TM: Operated group treated with pentoxifylline, liver

We claim:
1. A method of accelerating a healing process of an anastomosis in a mammalian subject with said anastomosis, which comprises the step of administering to said mammalian subject a therapeutically effective amount of a compound selected from the group consisting of:
3,7-dihydro-3,7-dimethyl-1-(5-oxohexyl)-1H-purine-2,6-dione;
1-(3',4'-diethoxybenzyl)-6,7-diethoxy-3,4-dihydro-isoquinolinium-theophylline-7-acetate or its monohydrate; and
mixtures thereof.

2. The method of accelerating a healing process of an anastomosis defined in claim 1 wherein the compound is administered parenterally.

3. A pharmaceutical composition for accelerating a healing process of an anastomosis which comprises a therapeutically effective amount of a mixture of:
3,7-dihydro-3,7-dimethyl-1-(5-oxohexyl)-1H-purine-2,6-dione; and
1-(3',4'-diethoxybenzyl)-6,7-diethoxy-3,4-dihydro-isoquinolinium theophylline-7-acetate or its monohydrate; in combination with a pharmaceutically acceptable inert carrier.

4. A method of treatment for improving tissue antioxidant status of a mammalian subject in need of said treatment, which comprises the step of administering to said mammalian subject a therapeutically effective amount of
1-(3',4'-diethoxybenzyl)-6,7-diethoxy-3,4-dihydro-isoquinolinium theophylline-7-acetate or its monohydrate; or a therapeutically effective amount of a mixture of
3,7-dihydro-3,7-dimethyl-1-(5-oxohexyl)-1H-purine-2,6-dione; and
1-(3',4'-diethoxybenzyl)-6,7-diethoxy-3,4-dihydroisoquinolinium theophylline-7-acetate or its monohydrate.

* * * * *